VARIETY OF THE MILKWEED PLANT FAMILY

Filed July 31, 1968 2 Sheets-Sheet 1

INVENTOR,
LLOYD S. MAGNUSON by Roger L. Martin ATTORNEY

VARIETY OF THE MILKWEED PLANT FAMILY

Filed July 31, 1968 2 Sheets-Sheet 2

INVENTOR,
LLOYD S. MAGNUSON by Roger L. Martin ATTORNEY

United States Patent Office

Plant Pat. 3,008

Patented Dec. 8, 1970

3,008

VARIETY OF THE MILKWEED PLANT FAMILY

Lloyd S. Magnuson, Leesburg, Fla., assignor to B. L. Cobia, Inc., Winter Garden, Fla., a corporation of Florida Filed July 31, 1968, Ser. No. 749,220
Int. Cl. A01h 5/00
U.S. Cl. Plt.—88 1 Claim

ABSTRACT OF THE DISCLOSURE

A new and distinct plant variety of the milkweed family developed from a mutation that appeared on a plant of the *Hoya Carnosa Exotica* variety is distinguished from its antecedents and known related varieties by a growth habit which combines the following distinctive characteristics:

Figure 1:
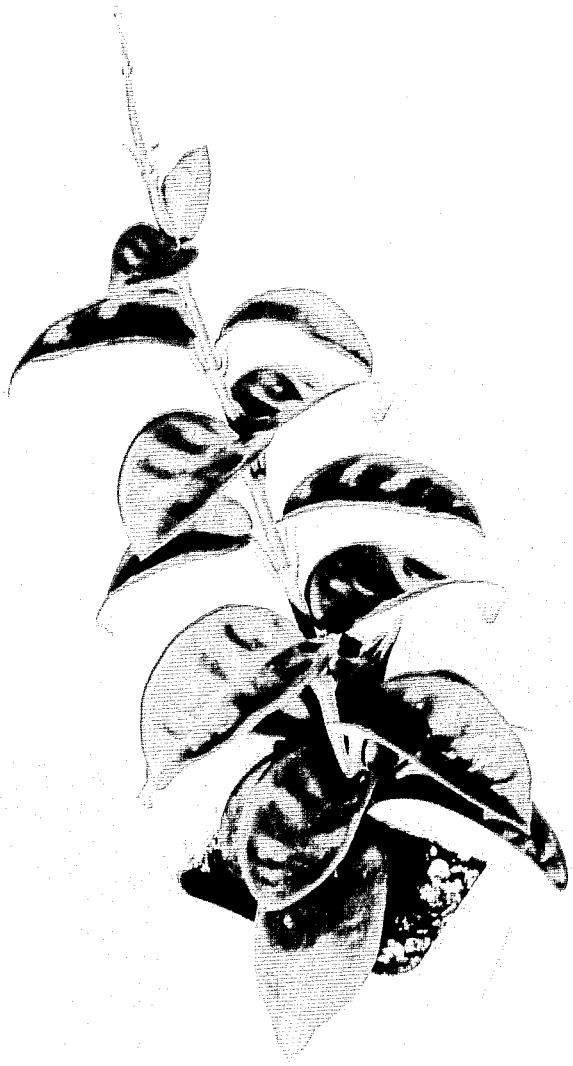
Figure 2:
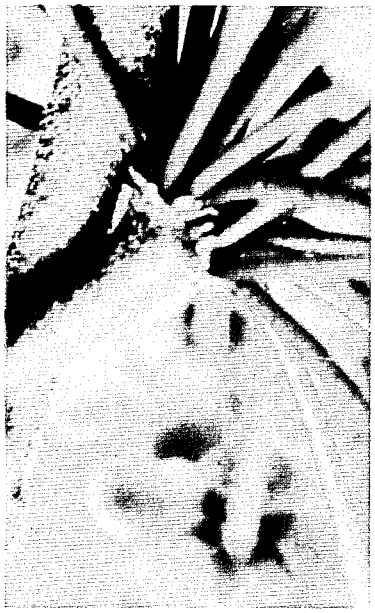
Figure 3:
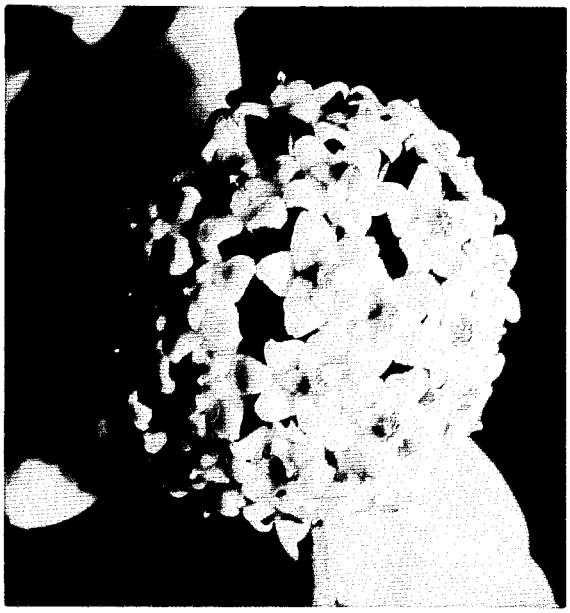
Figure 4:
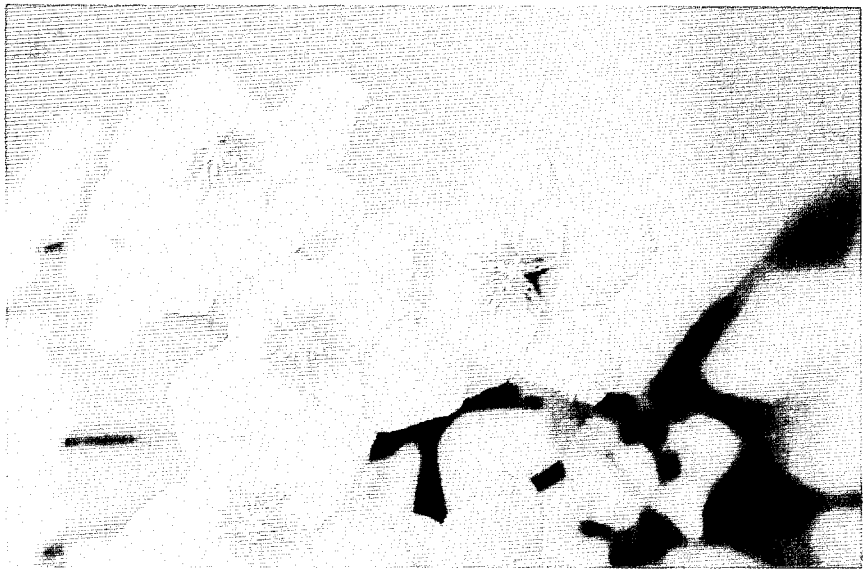

(1) Leaf blades which have a solid green field and are broader in comparison to the parent variety, and which are wrinkled in appearance by dimples or depressions that occur in the upper surface of the leaf blade at opposite sides of midrib and with the depressions or dimples usually numbering from 6 to 10 in each blade,
(2) Stems, peduncles, and pedicels which are thicker in comparison to the parent variety and with the lengths of the peduncles and distances between nodes being shorter in comparison to the parent variety,
(3) Stems and peduncles which in color range from moderate olive brown to grayish reddish brown,
(4) Petioles which in color range from moderate olive to moderate yellow green, and
(5) Pedicels which in color range from strong brown to grayish reddish orange.

The invention relates to a new and distinct plant variety of the milkweed (Asclepiadaceae) family which has been developed from a mutation that appeared on the plant of the *Hoya Carnosa Exotica* variety.

The principal objective of the invention has been to develop a healthy robust appearing new plant variety for the foliage plant market and which is related to the *Hoya Carnosa Exotica* variety and distinguishable from it and other related varieties that are currently being offered in the market place.

The new variety, in constrast to the growth habit of its parent, has a healthier more robust appearance. This is in part attributed to a growth habit which provides somewhat thicker stems that have a shorter distance between nodes than the parent and which also provides broader leaf blades that have a solid green field in contrast to the variegated type leaf blade found in the parent variety.

The new variety has been asexually reproduced in a nursery at Leesburg, Fla., by the propagation of stem cuttings taken from the mutation. Through successive propagations, the new variety has been found to be distinguishable from its antecedents and related varieties known to the inventor by a growth habit which combines the following distinctive characteristics:

(1) Leaf blades which have a solid green field and are broader in comparison to the parent variety and which are wrinkled in appearance by dimples or depressions that occur in the upper surfaces of the leaf blade at opposite sides of midrib and with the depressions or dimples usually numbering from six to ten in each blade,
(2) Stems, peduncles and pedicels which are thicker in comparison to the parent variety and with the lengths of the peduncles and distances between nodes being shorter in comparison to the parent variety,
(3) Stems and peduncles which in color range from moderate olive brown to grayish reddish brown,
(4) Petioles which in color range from moderate olive to moderate yellow green, and
(5) Pedicels which in color range from strong brown to grayish reddish orange.

The accompanying drawings serve by color photographic means to illustrate the new variety and wherein;

FIG. I shows a potted specimen of the new variety,

FIG. II shows a stem together with a peduncle and attached pedicels of an infloresence of a specimen of the new variety, FIG. III shows a flower cluster of a specimen, and FIG. IV is an enlargement of some of the flowers shown in FIG. III.

The following is a detailed description of the new variety and is based on observations of well fertilized specimens which were grown in the Central Florida area under 85% shaded nursery conditions and where temperatures range from about 60° F. to about 85° F. during the winter months and from about 75° F. to about 95° F. during the summer months. Except where general terms of ordinary dictionary significance are obviously used, color terminology and color designations reported herein are in accord with the ISCC-NBS method of designating colors as described in the U.S. Department of Commerce, National Bureau of Standards, Circular 553, entitled "The ISCC-NBS Method of Designating Colors and a Dictionary of Color Names" with the color designations having been derived through interpretation of Munsell Color Notations obtained by comparing specimens with color specimens in the current Neighboring Hues Edition of the Munsell Book of Color, published by Munsell Color Company, Inc. of Baltimore, Md. and to which the reported color notations (Munsell Hue/Munsell Value/Munsell Chroma) are referenced.

*Plant description*

Name: Hoya Carnosa (cv) Krinkle 8
Parentage: *Hoya Carnosa Exotica*
Classification:
- A. *Botanic.*—(Asclepiadaceae) milkweed family.
- B. *Commercial.*—Foliage plant.
- *Form.*—Semisucculent, tropical, twining vine type perennial evergreen with some branching.

Stems:
- A. *General.*—Caulescent, fleshy, herbaceous.
- B. *Texture.*—Moderately pubescent during immaturity and with age becoming glabrous and ultimately covered with thick waxy scale.
- C. *Size.*—(1) Diameter—usually 3–5 mm. at maturity. (2) Internode—usually 20–45 mm. and usually somewhat shorter near the root end of the stem.
- D. *Color.*—Ranges from moderate olive brown to grayish reddish brown between plant specimens and with some variation in any one specimen. Commonly grayish brown (5 YR 4/2), (5 YR 3/2), (7.5 YR 4/2), moderate brown (7.5 YR 4/4), moderate yellowish brown (10 YR 4/4) and grayish yellowish brown (10 YR 4/2), and occasionally grayish reddish brown (2.5 YR 3/2) or moderate olive brown (2.5 Y 4/2).

Leaves:
- A. *General.*—simple, exstipulate.
- B. *Arrangement.*—opposite.
- C. *Margins.*—entire.
- D. *Venation.*—pinnate.
- E. *Shape.*—(1) General—ovate. (2) Leaf apices— acute with acuminate tendency. (3) Leaf Bases—cordate.

F. *Petioles.*—(1) General—herbaceous, fleshy. (2) Texture—slightly pubescent and with age becoming glabrous and ultimately covered with moderately thick waxy scale. (3) Size: (a) Diameter—usually 2–5 mm. at maturity. (b) Length—10–25 mm. at maturity. (4) Color: ranges from moderate olive to moderate yellow green between plant specimens and between leaves in any one specimen with the petiole side nearest the stem usually tending to be darker than the other side. Commonly moderate olive (5 Y 4/4), light olive (7.5 Y 5/4) (10 Y 5/6) and moderate olive green (2.5 GY 6/6).

G. *Leaf blades.*—(1) General—semisucculent with wrinkled blade caused by depressions or dimples in the surface at the upper epidermis side of blade and which provide rises in the surface at the lower epidermis side of blade, the depressions or dimples being at opposite sides of the midrib and usually numbering from 6 to 10 in each leaf blade. (2) Texture: (a) Upper epidermis—slightly pubescent during immaturity and becoming glabrous with smooth waxy surface during maturity. (b) Lower epidermis—moderately pubescent and heavily glacous. (3) Size: (a) Length—usually 5–8 cm. at maturity. (b) Width—usually 2.5–4.5 cm. at maturity. (4) Color—(a) Upper epidermis—continuous or solid green field which between plant specimens and leaves of one specimen is commonly moderate yellow green (5 GY 6/6), (5 GY 5/6), strong yellow green (5 GY 6/8) or moderate olive green (7.5 GY 4/6). (b) Lower epidermis—continuous field which between plant specimens and leaves of one specimen is commonly light yellow green (5 GY 8/4) or moderate yellow green (5 GY 7/6), (5 GY 6/6).

Inflorescence form.—Simple umbel with minute 5-merous bracts and usually 20–35 flowers in a cluster.

Peduncles:

A. *General.*—hard, fleshy.

B. *Texture.*—slightly pubescent and with age becoming glabrous and ultimately covered with moderately thick waxy scale.

C. *Size.*—(1) Length—usually 10–25 mm. (2) Diameter—usually 2.5–4 mm.

D. *Color.*—ranges from moderate olive brown to grayish reddish brown between plant specimens and with some variation in any one specimen. Commonly grayish brown (5 YR 4/2), (5 YR 3/2), (7.5 YR 4/2), moderate brown (7.5 YR 4/4), moderate yellowish brown (10 YR 4/4) and grayish yellowish brown (10 YR 4/2), and occasionally grayish reddish brown (2.5 YR 3/2) or moderate olive brown (2.5 Y 4/2).

Pedicels:

A. *General.*—soft, fleshy.

B. *Texture.*—pubescent.

C. *Size.*—(1) Length—usually 20–25 mm. (2) Diameter—usually about 1 mm.

D. Color.—Ranges from strong brown ( to grayish reddish orange (2.5 YR 5/6).

Flowers:

A. *General.*—complete, perfect, actinomorphic and 5-merous type flower with hypogynous perianth and alternate sepal-petal and petal-corona segment arrangements.

B. *Size.*—Diameter—usually 16–19 mm.

C. *Calyx.*—(1) General—5-merous with separate, valvate sepais. (2) Sepal texture—(a) Upper epidermis—glabrous. (b) Lower epidermis—moderately pubescent, (3) Septal size—(a) Proximal to distal end length—about 2 mm. (4) Sepal color—

(a) Upper epidermis—continuous field and usually moderate red (2.5 R 5/8), dark pink (10 RP 6/6, (2.5 R 6/6), or grayish purplish red (10 RP 5/6). (b) Lower epidermis—continuous field and usually dark pink (10 RP 6/6), (2.5 R 6/6), or grayish red (2.5 R 5/6).

D. *Corolla.*—(1) General—5-merous, valvate and rotate with interpetal basal fusion for about ½ petal length. (2) Petal texture—(a) Upper epidermis—very dense velvety pubescent. (b) Lower epidermis—glabrous and waxy. (3) Petal size—(a) Proximal to distal end length—about 8 mm. (4) Petal color—(a) Upper epidermis—continuous field and usually light moderate pink (2.5 R 8/4), (10 RP 8/4), or pale purplish pink (7.5 RP 8/4). (b) Lower epidermis—continuous field and usually light moderate pink (2.5 R 8/4), (10 RP 8/4) or pale purplish pink (7.5 RP 8/4).

E. *Corona.*—(1) General—5-merous horn-like segments which are adnate to stigma and corolla and crested at their proximal ends. (2) Segment texture—hard. Smooth, waxy and glabrous. (3) Segment size—(a) Proximal to distal end length—about 4 mm. (b) Maximum width—about 2.5 mm. (4) Segment color— (a) Proximal end—moderate purplish red (10 RP 4/8) or dark purplish red (10 RP 3/6) and merging with distal end color. (b) Distal end—pale yellow green (near 10 Y 9/2) and merging with proximal end color.

F. *Androecium.*—(1) General—5-merous pollinium pairs partially enclosed by expanded translucent perenchymatous translators and attached to stigma through corpuscula located between adjacent segment and with pollinia and translators rising above corpuscula and stigma in converging conical arrangement. (2) Pollinium color—vivid yellow (5 Y 8/12).

G. *Gynoecium.*—(1) General—compound and apocarpous pistil with common stigma. (2) Stigma—(a) General—5-lobed and waxy. (b) Stigma color—light—moderate orange yellow (10 YR 8/8) or light moderate brilliant strong yellow (2.5 Y 8/8). (3) Style—lacking. (4) Ovary—(a) General—2 monocarpellate ovullaries with axillary placentation of ovules. (b) Size—length about 2 mm. (c) Color—grayish red (5 R 5/6).

Growth habit: Vigorous in tropical and semitropical environments with some branching and principal distinctive characteristics previously mentioned.

The following is a description of a typical plant specimen grown in the Central Florida area under the conditions indicated heretofore.

Age: 10 mos. from propagation of cutting.
Vine length: 254 cm.
No. of nodes: 12.
No. of mature leaves: 15.
No. of immature leaves. 4.
No. of embrionic leaves: 4.

Stem:

(1) *Diameter.*—Ranges from 4 mm. near root to 2 mm. at 2.5 cm. from stem tip.

(2) *Internode distance.*—21 mm. (av.).

(3) *Color.*—Moderate brown (7.5 YR 4/4).

Leaves:

(1) *Petioles.*—(Nonembrionic)—(a) Diameter —3 mm. (av.). (b) Length—ranges from 13–18 mm. (c) Color—light olive (7.5 Y 5/4).

(2) *Blades.*—(Nonembrionic)—(a) Length—ranges from 60–77 mm. (b) Width—ranges from 30–35 mm. (c) Color—(1) Upper epidermis—moderate olive green (7.5 GY 4/6). (2) Lower epidermis—moderate yellowish green (5 GY 7/6). (d) Dimples—ranges from 7–10 per blade.

The following is a description of a typical flower cluster that developed in a plant specimen grown in the Central Florida area under the conditions indicated heretofore.

*Peduncle.*—(1)Age—about 1 year. (2) Length—18 mm. (3) Diameter—about 3 mm. (4) Color—grayish brown (7.5 YR 4/2).

*Pedicels.*—(1) Number—27. (2) Length—21 mm. (av.). (3) Diameter—about 1 mm. (4) Color—strong brown (2.5 YR 4/6).

*Flowers.*—(1) Number—27. (2) Diameter—about 18 mm. (av.). (3) Calyx—(a) Sepal size—proximal end to distal end length—about 2 mm. (av.). Sepal color—(1) Upper epidermis—dark pink (10 RP 6/6). (2) Lower epidermis—dark pink (10 RP 6/6). (4) Corolla—(a) Petal size—proximal to distal end length—about 8 mm. (av.). (b) Petal color—(1) Upper epidermis—pale purplish pink (7.5 RP 8/4). (2) Lower epidermis—pale purplish pink (7.5 RP 8/4). (5) Corona—(a) Segment size—(1) Proximal to distal end length—about 4 mm. (av.). (2) Maximum width—about 2.5 mm. (b) Segment color—(1) Proximal end—dark purplish red (10 RP 3/6). (2) Distal end—pale yellow green (near 10 Y 9/2). (c) Pollinium color—vivid yellow (5 Y 8/12). (d) Stigma color—light moderate orange yellow (10 YR 8/8. (e) Ovary size—length about 2 mm. (av.). (f) Ovary color—grayish red (5 R 5/6).

In contrast to the open leaf blade characteristics of the new variety and which are evident in FIG. 1, leaf blades of the *Hoya Carnosa Compacta* variety are distinguishable in that they have strong conduplicate and recurved tendencies which commonly result in nearly closed blades with bent midribs that draw the apices of the blades toward the plant stem. Among other characteristics which distinguish plants of the new variety from those of the *Hoya Carnosa Compacta* variety are those providing longer and larger diameter pedicels in plants of the new variety, as well as flowers of a greater diameter than those of the *Hoya Carnosa Compacta* variety.

I claim:

1. The new and distinct variety of the milkweed family, substantially as herein shown and described, characterized in particular as to novelty by a growth habit that combines the following distinctive characteristics:

(1) leaf blades which have a solid green field and are wrinkled in appearance by depressions at opposite sides of the midrib that usually number from six to ten in each mature blade and which are broader in comparison to leaf blades of the *Hoya Carnosa Exotica* variety, (2) stems, peduncles and pedicels which are thicker in comparison to those of the *Hoya Carnosa Exotica* variety and with the peduncle lengths and internode distances being shorter in comparison to those of the *Hoya Carnosa Exotica* variety, (3) stems and peduncles which in color range from moderate olive brown to grayish reddish brown, (4) petioles which in color range from moderate olive to moderate yellow green, and (5) pedicels which in color range from strong brown to grayish reddish orange.

References Cited

Orchids, Alberts & Merkel Bros., Inc., 1963, Boynton Beach, Fla., p. 87 relied on, copy in Gp 337 at Examiner's desk.

ROBERT E. BAGWILL, Primary Examiner

PO-1050
(5/69)

UNITED STATES PATENT OFFICE
CERTIFICATE OF CORRECTION

Patent No. Plant Pat. 3008 Dated December 8, 1970

Inventor(s) Lloyd S. Magnuson

It is certified that error appears in the above-identified patent and that said Letters Patent are hereby corrected as shown below:

Column 3, Line 63, after "brown (" insert -- 2.5 YR 4/6) --;
Column 5, Line 13, before "Sepal" insert -- (b) --;

SIGNED AND
SEALED
MAR 9 1971

(SEAL)
Attest:

Edward M. Fletcher, Jr.
Attesting Officer

WILLIAM E. SCHUYLER, JR.
Commissioner of Patents